US006184442B1

(12) United States Patent
Nickell

(10) Patent No.: US 6,184,442 B1
(45) Date of Patent: Feb. 6, 2001

(54) SOYBEAN CULTIVAR 9323265446452

(75) Inventor: Andrew D. Nickell, Milton, WI (US)

(73) Assignee: Asgrow Seed Company LLC, Des Moines, IA (US)

(*) Notice: Under 35 U.S.C. 154(b), the term of this patent shall be extended for 0 days.

(21) Appl. No.: 09/478,499

(22) Filed: Jan. 6, 2000

(51) Int. Cl.[7] .............................. A01H 5/00; A01H 5/10; A01H 1/02; C12N 5/04

(52) U.S. Cl. ........................... 800/312; 800/260; 435/415

(58) Field of Search ................................... 800/312, 260; 435/415

(56) References Cited

U.S. PATENT DOCUMENTS 5,945,588 * 8/1999 Nickell .................................. 800/312

* cited by examiner

*Primary Examiner*—Elizabeth F. McElwain
(74) *Attorney, Agent, or Firm*—Rothwell, Figg, Ernst & Manbeck

(57) ABSTRACT

A novel soybean cultivar, designated 9323265446452, is disclosed. The invention relates to the seeds of soybean cultivar 9323265446452, to the plants of soybean 9323265446452 and to methods for producing a soybean plant produced by crossing the cultivar 9323265446452 with itself or another soybean variety. The invention further relates to hybrid soybean seeds and plants produced by crossing the cultivar 9323265446452 with another soybean cultivar.

23 Claims, No Drawings

SOYBEAN CULTIVAR 9323265446452

BACKGROUND OF THE INVENTION

The present invention relates to a new and distinctive soybean cultivar, designated 9323265446452. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior soybean cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same soybean traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new soybean cultivars.

The development of new soybean cultivars requires the development and selection of soybean varieties, the crossing of these varieties and selection of superior hybrid crosses. The hybrid seed is produced by manual crosses between selected male-fertile parents or by using male sterility systems. These hybrids are selected for certain single gene traits such as pod color, flower color, pubescence color or herbicide resistance which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Soybean, *Glycine max* (L), is an important and valuable field crop. Thus, a continuing goal of plant breeders is to develop stable, high yielding soybean cultivars that are agronomically sound. The reasons for this goal are obviously to maximize the amount of grain produced on the land used and to supply food for both animals and humans. To accomplish this goal, the soybean breeder must select and develop soybean plants that have the traits that result in superior cultivars.

SUMMARY OF THE INVENTION

According to the invention, there is provided a novel soybean cultivar, designated 9323265446452. This invention thus relates to the seeds of soybean cultivar 9323265446452, to the plants of soybean 9323265446452 and to methods for producing a soybean plant produced by crossing the soybean 9323265446452 with itself or another soybean line.

Thus, any such methods using the soybean variety 9323265446452 are part of this invention: selfing, backcrosses, hybrid production, crosses to populations, and the like. All plants produced using soybean variety 9323265446452 as a parent are within the scope of this invention. Advantageously, the soybean variety could be used in crosses with other, different, soybean plants to produce first generation ($F_1$) soybean hybrid seeds and plants with superior characteristics.

In another aspect, the present invention provides for single gene converted plants of 9323265446452. The single transferred gene may preferably be a dominant or recessive allele. Preferably, the single transferred gene will confer such traits as herbicide resistance, insect resistance, resistance for bacterial, fungal, or viral disease, male fertility, male sterility, enhanced nutritional quality, and industrial usage. The single gene may be a naturally occurring soybean gene or a transgene introduced through genetic engineering techniques.

In another aspect, the present invention provides regenerable cells for use in tissue culture of soybean plant 9323265446452. The tissue culture will preferably be capable of regenerating plants having the physiological and morphological characteristics of the foregoing soybean plant, and of regenerating plants having substantially the same genotype as the foregoing soybean plant. Preferably, the regenerable cells in such tissue cultures will be embryos, protoplasts, meristematic cells, callus, pollen, leaves, anthers, roots, root tips, flowers, seeds, pods or stems. Still further, the present invention provides soybean plants regenerated from the tissue cultures of the invention.

DEFINITIONS

In the description and tables which follow, a number of terms are used. In order to provide a clear and consistent understanding of the specification and claims, including the scope to be given such terms, the following definitions are provided:

Maturity Date. Plants are considered mature when 95% of the pods have reached their mature color. The number of days are either calculated from August 31 or from the planting date.

Seed Yield (Bushels/Acre). The yield in bushels/acre is the actual yield of the grain at harvest.

Lodging Resistance. Lodging is rated on a scale of 1 to 5. A score of 1 indicates erect plants. A score of 2.5 indicates plants are leaning at a 450° angle in relation to the ground and a score of 2.5 indicates plants are laying on the ground.

Phytophthora Tolerance. Tolerance to Phytophthora root rot is rated on a scale of 1 to 5, with a score of 1 being the best or highest tolerance ranging down to a score of 5 which indicates the plants have no tolerance to Phytophthora.

Emergence. This score indicates the ability of the seed to emerge when planted 3" deep in sand and with a controlled temperature of 25° C. The number of plants that emerge each day are counted. Based on this data, each genotype is given a 1 to 5 score based on its rate of emergence and percent of emergence. A score of 1 indicates an excellent rate and percent of emergence, an intermediate score of 2.5 indicates average ratings and a 5 score indicates a very poor rate and percent of emergence.

Iron-Deficiency Chlorosis. Plants are scored 1 to 5 based on visual observations. A score of 1 means no stunting of the plants or yellowing of the leaves and a score of 5 indicates the plants are dead or dying caused by iron-deficiency chlorosis, a score of 2.5 means plants have intermediate health with some leaf yellowing.

Brown Stem Rot. This is a visual disease score from 1 to 5 comparing all genotypes in a given test. The score is based on leaf symptoms of yellowing and necrosis caused by brown stem rot. A score of 1 indicates no symptoms. Visual scores range to a score of 5 which indicates severe symptoms of leaf yellowing and necrosis.

Shattering. The amount of pod dehiscence prior to harvest. Pod dehiscence involves seeds falling from the pods to the soil. This is a visual score from 1 to 5 comparing all genotypes within a given test. A score of 1 means pods have not opened and no seeds have fallen out. A score of 2.5 indicates approximately 50% of the pods have opened, with seeds falling to the ground and a score of 5 indicates 100% of the pods are opened.

Plant Height. Plant height is taken from the top of soil to top node of the plant and is measured in inches.

Seed Protein Peroxidase Activity. Seed protein peroxidase activity is defined as a chemical taxonomic technique to separate cultivars based on the presence or absence of the peroxidase enzyme in the seed coat. There are two types of soybean cultivars, those having high peroxidase activity (dark red color) and those having low peroxidase activity (no color).

Allele. Allele is any of one or more alternative forms of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Essentially all the physiological and morphological characteristics. A plant having essentially all the physiological and morphological characteristics means a plant having the physiological and morphological characteristics, except for the characteristics derived from the converted gene.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Single Gene Converted (Conversion). Single gene converted (conversion) plant refers to plants which are developed by a plant breeding technique called backcrossing wherein essentially all of the desired morphological and physiological characteristics of a variety are recovered in addition to the single gene transferred into the variety via the backcrossing technique or via genetic engineering.

DETAILED DESCRIPTION OF THE INVENTION

Soybean cultivar 9323265446452 has superior characteristics and was developed from the cross A2833/A2722/ A2835/A3237/3/40-3-2. $F_1$ and $F_2$ plants were advanced by a modified single seed descent selection. $F_3$ derived $F_4$ lines were selected in 1995. $F_3$ derived $F_5$ seed was grown in 1996 for increase. In 1997 the line was tested at 10 Midwest locations.

9323265446452 is a mid maturity group II variety with very high yield potential to lines of similar maturity and has excellent agronomic characteristics, including lodging resistance. 9323265446452 is resistant to the RoundUp™ herbicides and has a major gene for Phytophthora resistance, Rps1k, conferring resistance to most races of Phytophthora Root Rot. 9323265446452 is well adapted to the mid maturity group II growing areas of Michigan, Iowa, Illinois, Minnesota and Wisconsin.

Some of the criteria used to select in various generations include: seed yield, lodging resistance, emergence, disease tolerance, maturity, late season plant intactness, plant height and shattering resistance.

The cultivar has shown uniformity and stability, as described in the following variety description information. It has been self-pollinated a sufficient number of generations with careful attention to uniformity of plant type. The line has been increased with continued observation for uniformity.

Soybean cultivar 9323265446452 has the following morphologic and other characteristics (based primarily on data collected at Janesville, Wis.).

VARIETY DESCRIPTION INFORMATION

1. Seed Shape: Spherical Flattened (L/NW ratio >1.2; L/T ratio =<1.2)
2. Hilum Color: (Mature Seed)—Imperfect Black
3. Pod color Brown
4. Seed Coat Luster: Dull
5. Seed Coat Color: Yellow
6. Flower Color: Purple
7. Leaflet Shape: Ovate
8. Leaflet Size: Medium
9. Leaf Color: Medium-green
10. Plant Pubescence Color: Gray
11. Plant Habit: Indeterminate
12. Maturity Group: II
13. Relative Maturity: 2.6
14. Physiological Responses:
    Roundup Ready™ Herbicide: Resistant
15. Disease Resistance:

| Phytophthora Rot (*Phytophthora megasperma* var. *sojae*): | |
|---|---|
| Race 1 | Resistant |
| Race 2 | Resistant |
| Race 3 | Resistant |
| Race 4 | Resistant |
| Race 5 | Resistant |
| Race 6 | Resistant |
| Race 7 | Resistant |
| Race 8 | Resistant |
| Race 9 | Resistant |
| Race 10 | Resistant |
| Race 11 | Resistant |
| Race 13 | Resistant |
| Race 14 | Resistant |
| Race 15 | Resistant |
| Race 17 | Resistant |

-continued

Phytophthora Rot (*Phytophthora megasperma* var. *sojae*):

| | |
|---|---|
| Race 18 | Resistant |
| Race 22 | Resistant |
| Race 24 | Resistant |

This invention is also directed to methods for producing a soybean plant by crossing a first parent soybean plant with a second parent soybean plant, wherein the first or second soybean plant is the soybean plant from the line 9323265446452. Further, both first and second parent soybean plants may be from the cultivar 9323265446452. Therefore, any methods using the cultivar 9323265446452 are part of this invention: selfing, backcrosses, hybrid breeding, and crosses to populations. Any plants produced using cultivar 9323265446452 as a parent are within the scope of this invention.

As used herein, the term "plant" includes plant cells, plant protoplasts, plant cells of tissue culture from which soybean plants can be regenerated, plant calli, plant clumps, and plant cells that are intact in plants or parts of plants, such as pollen, flowers, embryos, ovules, seeds, pods, leaves, stems, roots, anthers and the like. Thus, another aspect of this invention is to provide for cells which upon growth and differentiation produce a cultivar having essentially all of the physiological and morphological characteristics of 9323265446452.

Culture for expressing desired structural genes and cultured cells are known in the art. Also as known in the art, soybeans are transformable and regenerable such that whole plants containing and expressing desired genes under regulatory control may be obtained. General descriptions of plant expression vectors and reporter genes and transformation protocols can be found in Gruber, et al., "Vectors for Plant Transformation, in Methods in Plant Molecular Biology & Biotechnology" in Glich, et al., (Eds. pp. 89–119, CRC Press, 1993). Moreover GUS expression vectors and GUS gene cassettes are available from Clone Tech Laboratories, Inc., Palo Alto, Calif. while luciferase expression vectors and luciferase gene cassettes are available from Pro Mega Corp. (Madison, Wis.). General methods of culturing plant tissues are provided for example by Maki, et al., "Procedures for Introducing Foreign DNA into Plants" in Methods in Plant Molecular Biology & Biotechnology, Glich, et al., (Eds. pp. 67–88 CRC Press, 1993); and by Phillips, et al., "Cell-Tissue Culture and In-Vitro Manipulation" in Corn & Corn Improvement, 3rd Edition; Sprague, et al., (Eds. pp. 345–387) American Society of Agronomy Inc., 1988. Methods of introducing expression vectors into plant tissue include the direct infection or cocultivation of plant cells with *Agrobacterium tumefaciens*, Horsch et al., Science, 227:1229 (1985). Descriptions of Agrobacterium vectors systems and methods for Agrobacterium-mediated gene transfer provided by Gruber, et al., supra.

Useful methods include but are not limited to expression vectors introduced into plant tissues using a direct gene transfer method such as microprojectile-mediated delivery, DNA injection, electroporation and the like. More preferably expression vectors are introduced into plant tissues using the microprojectile media delivery with the biolistic device Agrobacterium-medicated transformation. Transforrnant plants obtained with the protoplasm of the invention are intended to be within the scope of this invention.

The present invention contemplates a soybean plant regenerated from a tissue culture of a variety (e.g., 9323265446452) or hybrid plant of the present invention. As is well known in the art, tissue culture of soybean can be used for the in vitro regeneration of a soybean plant. Tissue culture of various tissues of soybeans and regeneration of plants therefrom is well known and widely published. For example, reference may be had to Komatsuda, T., et al., "Genotype X Sucrose Interactions for Somatic Embryogenesis in Soybean," Crop Sci. 31:333–337 (1991); Stephens, P. A., et al., "Agronomic Evaluation of Tissue-Culture-Derived Soybean Plants," Theor. Appl. Genet. (1991) 82:633–635; Komatsuda, T., et al., "Maturation and Germination of Somatic Embryos as Affected by Sucrose and Plant Growth Regulators in Soybeans *Glycine gracilis* Skvortz and *Glycine max* (L.) Merr.," Plant Cell, Tissue and Organ Culture, 28:103–113 (1992); Dhir, S., et al., "Regeneration of Fertile Plants from Protoplasts of Soybean (*Glycine max* L. Merr.): Genotypic Differences in Culture Response, "Plant Cell Reports (1992) 11:285–289; Pandey, P. et al., "Plant Regeneration from Leaf and Hypocotyl Explants of *Glycine wightii* (W. And A.) VERDC. var longicauda," Japan J. Breed. 42:1–5 (1992); and Shetty, K., et al., "Stimulation of In Vitro Shoot Organogenesis in *Glycine max* (Merrill.) by Allantoin and Amides," Plant Science (1992) 81:245–251; as well as U. S. Pat. No. 5,024,944, issued Jun. 18, 1991 to Collins, et al., and U. S. Pat. No. 5,008,200, issued Apr.16, 1991 to Rauch, et al., the disclosures of which are hereby incorporated herein in their entirety by reference. Thus, another aspect of this invention is to provide cells which upon growth and differentiation produce soybean plants having the physiological and morphological characteristics of variety 9323265446452.

The cultivar 9323265446452 is similar to A2722. While similar to A2722, there are numerous differences including: 9323265446452 has the gene for resistance to the Roundup herbicides and A2722 does not contain this gene. Additionally, 9323265446452 has a gray pubescence and imperfect black hilum while A2722 is tawny and black, respectively.

TABLES

In Tables 1, 2 and 3 that follows, the traits and characteristics of soybean cultivar 9323265446452 are compared to several competing varieties of commercial soybeans of similar maturity. In the tables, column 1 shows the yield in bushels/acre for the instant invention and the Competitor Variety. Column 2 indicates the days to maturity after August 31 for the instant invention and the Competitor Variety. Column 3 shows the plant height in inches for the instant invention and the Competitor Variety. Column 4 indicates the plant lodging for the instant invention and the Competitor Variety. Column 5 shows the general appearance rating scores for the instant invention and the Competitor Variety. Lodging and General Appearance Rating scores are rated 1=Best and 5=Worst.

TABLE 1

1996 AGRONOMIC DATA

| | BU/A | MAT | HGT | LDG | GR |
|---|---|---|---|---|---|
| Overall Mean | 50.41 | 23.00 | 28.70 | 1.30 | 2.40 |
| Number of Locations | 3 | 3 | 3 | 3 | 3 |
| 9323265446452 | 63.35 | 27.00 | 32.30 | 1.20 | 2.30 |
| Stine 2250 | 56.85 | 24.00 | 28.70 | 1.20 | 2.30 |
| Asgrow A2242 | 53.04 | 23.00 | 28.70 | 1.20 | 1.70 |
| Asgrow A1900 | 50.71 | 19.00 | 25.30 | 1.50 | 2.00 |

TABLE 2

1997 AGRONOMIC DATA

|  | BU/A | MAT | HGT | LDG | GR |
|---|---|---|---|---|---|
| Overall Mean | 61.80 | 23.30 | 32.60 | 1.50 | 2.60 |
| Number of Locations | 10 | 11 | 11 | 9 | 11 |
| LSD | 1.81 | 0.94 | 1.10 | 0.24 | 0.28 |
| 9323265446452 | 65.46 | 24.50 | 32.10 | 1.20 | 2.10 |

TABLE 2-continued

1997 AGRONOMIC DATA

|  | BU/A | MAT | HGT | LDG | GR |
|---|---|---|---|---|---|
| Asgrow AG2702 | 64.74 | 25.10 | 36.20 | 2.10 | 2.90 |
| Asgrow AG3002 | 63.58 | 28.10 | 33.40 | 1.90 | 2.90 |
| Asgrow AG2401 | 60.40 | 21.10 | 30.60 | 1.40 | 2.40 |

TABLE 3

1998 AGRONOMIC DATA

|  | BU/A | MAT | HGT | LDG | GR |
|---|---|---|---|---|---|
| Overall Mean | 64.88 | 18.00 | 36.00 | 1.80 | 2.50 |
| Number of Locations | 22 | 22 | 22 | 21 | 22 |
| LSD | 1.51 | 0.49 | 0.72 | 0.14 | 0.19 |
| 9323265446452 | 69.69 | 16.80 | 36.60 | 1.60 | 2.50 |
| Asgrow AG2902 | 67.33 | 20.30 | 38.10 | 1.80 | 2.10 |
| Asgrow AG3002 | 64.91 | 20.70 | 36.40 | 2.30 | 3.00 |
| Asgrow AG2702 | 64.39 | 19.10 | 39.20 | 2.20 | 3.00 |
| Pioneer 9294 | 64.35 | 16.00 | 34.90 | 1.80 | 2.60 |
| Stine 2694 | 62.34 | 15.20 | 32.70 | 1.30 | 2.10 |
| Pioneer 92B71 | 61.64 | 15.60 | 32.90 | 1.50 | 2.40 |
| Stine 2254 | 61.20 | 15.20 | 32.80 | 1.40 | 2.20 |

In Table 4 that follows, the traits and characteristics of soybean cultivar 9323265446452 are compared to several competing varieties of commercial soybeans of similar maturity. Each characteristic also indicates the number of locations which comprise the figures given. In these tables, column 1 shows the Competitor Variety. In columns 2, 3, 4 and 5 show the number of sites, the yield in bushels/acre for the instant invention, the Competitor Variety identified in column 1 and the difference, respectively. Columns 6, 7 and 8 indicate the sites tested for days to maturity after August 31, for the instant invention and Competitor Variety, respectively. Columns 9, 10 and 11 show the number of sites tested for plant height in inches for the instant invention and the Competitor Variety respectively. Columns 12, 13 and 14 show the sites tested for plant lodging scores of the instant invention and Competitor Variety. Columns 15, 16 and 17 show the general rating scores for the instant invention and the Competitor Variety, respectively. Lodging and General Rating scores are rated 1=Best and 5=Worst.

TABLE 4

| Other Variety or Hybrid | Sites | Check Yield Bu/A | Other Yield Bu/A | Diff | Sites | Check Maturity >8/31 | Other Maturity >8/31 | Sites | Check Plt Ht In | Other Plt Ht In | Sites | Check Lodge (1–5) | Other Lodge (1–5) | Sites | Check GRat2 (1–5) | Other GRat2 (1–5) |
|---|---|---|---|---|---|---|---|---|---|---|---|---|---|---|---|---|
| Asgrow AG2401 | 12 | 60.7 | 55.5 | 5.2 | 12 | 25.0 | 21.8 | 10 | 1.2 | 1.3 | 11 | 32.3 | 30.9 | | | |
| Asgrow AG2702 | 41 | 64.1 | 60.3 | 3.8 | 38 | 19.6 | 21.4 | 35 | 1.6 | 2.2 | 38 | 35.3 | 37.7 | | | |
| Asgrow AG2902 | 29 | 65.5 | 63.1 | 2.3 | 26 | 17.2 | 20.6 | 25 | 1.7 | 1.9 | 27 | 36.5 | 37.8 | | | |
| Asgrow AG3002 | 41 | 64.1 | 61.2 | 2.8 | 38 | 19.6 | 23.4 | 35 | 1.6 | 2.2 | 38 | 35.3 | 35.3 | | | |
| Pioneer 9294 | 29 | 65.5 | 61.1 | 4.4 | 26 | 17.2 | 16.3 | 25 | 1.7 | 1.8 | 27 | 36.5 | 34.4 | | | |
| Pioneer 92B71 | 29 | 65.5 | 59.0 | 6.5 | 26 | 17.2 | 15.9 | 25 | 1.7 | 1.5 | 27 | 36.5 | 32.2 | | | |
| Stine 2254 | 29 | 65.5 | 58.3 | 7.2 | 26 | 17.2 | 15.6 | 25 | 1.7 | 1.5 | 27 | 36.5 | 32.4 | | | |
| Stine 2694 | 29 | 65.5 | 58.9 | 6.6 | 26 | 17.2 | 15.6 | 25 | 1.7 | 1.4 | 27 | 36.5 | 32.2 | | | |

When the term soybean plant is used in the context of the present invention, this also includes any single gene conversions of that variety. The term single gene converted plant as used herein refers to those soybean plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term backcrossing as used herein refers to the repeated crossing of a hybrid progeny back to the recurrent parent. The parental soybean plant which contributes the gene for the desired characteristic is termed the nonrecurrent or donor parent. This terminology refers to the fact that the nonrecurrent parent is used one time in the backcross protocol and therefore does not recur. The parental soybean plant to which the gene or genes from the nonrecurrent parent are transferred is known as the recurrent parent as it is used for several rounds in the backcrossing protocol (Poehiman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a soybean plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185, 5,973,234 and 5,977,445, the disclosures of which are specifically hereby incorporated by reference.

A further aspect of the invention relates to tissue culture of soybean plants designated 9323265446452. As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. (See U.S. Pat. Nos. 5,959,185; 5,973,234 and 5,977,445, the disclosures of which are incorporated herein by reference).

DEPOSIT INFORMATION

A deposit of the Asgrow Seed Company soybean cultivar 9323265446452, disclosed above and recited in the appended claims has been made with the American Type Culture Collection (ATCC), 10801 University Boulevard, Manassas, Va. 20110. The date of deposit was Oct. 6, 2000. The deposit of 2,500 seeds were taken from the same deposit maintained by Asgrow Seed Company since prior to the filing date of this application. All restrictions upon the deposit have been removed, and the deposti is intended to meet all of the requirements of 37 C.F.R. §1.801–1.809. The ATCC accession number is PTA-2577. The deposit will be maintained in the depository for a period of 30 years, or 5 years after the last request, or for the effective life of the patent, whichever is longer, and will be replaced as necessary duringthat period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A soybean seed designated 9323265446452, a sample of said seed deposited under ATCC Accession No. PTA-2577.

2. A plant, or parts thereof, produced by growing the seed of claim 1.

3. Pollen of the plant of claim 2.

4. An ovule of the plant of claim 2.

5. A soybean plant, or parts thereof, having all of the physiological and morphological characteristics of the soybean plant of claim 2.

6. A tissue culture of regenerable cells of a soybean plant of cultivar 9323265446452, wherein the tissue regenerates plants capable of expressing all of the morphological and physiological characteristics of the cultivar 9323265446452.

7. A tissue culture according to claim 6, the cells or protoplasts being from a tissue selected from the group consisting of leaves, pollen, embryos, meristematic cells, roots, root tips, anthers, flowers, seeds, stems and pods.

8. A soybean plant regenerated from the tissue culture of claim 6, capable of expressing all of the morphological and physiological characteristics of soybean cultivar 9323265446452.

9. A method for producing a soybean seed comprising crossing a first parent soybean plant with a second parent soybean plant and harvesting the resultant hybrid soybean seed, wherein said first or second parent soybean plant is the soybean plant of claim 2.

10. A hybrid soybean seed produced by the method of claim 9.

11. A hybrid soybean plant, or parts thereof, produced by growing said hybrid soybean seed of claim 10.

12. Soybean seed produced from said hybrid soybean plant of claim 11.

13. A method for producing a hybrid soybean seed comprising crossing a soybean plant according to claim 2 with a second soybean plant.

14. A hybrid soybean seed produced by the method of claim 13.

15. A hybrid soybean plant, or parts thereof, produced by growing said hybrid soybean seed of claim 14.

16. Soybean seed produced from said hybrid soybean plant of claim 15.

17. A method for producing a 9323265446452-derived soybean plant, comprising:

a) crossing soybean line 9323265446452, a sample of seed of said line having been deposited under ATCC accession No. PTA-2577, with a second soybean plant to yield progeny soybean seed;

b) growing said progeny soybean seed, under plant growth conditions, to yield said 9323265446452-derived soybean plant.

18. The method of claim 17, further comprising utilizing plant tissue culture methods to derive progeny of said 9323265446452-derived soybean plant and wherein the regenerated plant has all of the physiological and morphological characteristics of the plant of claim 17.

19. A method for developing a soybean plant in a soybean plant breeding program using plant breeding techniques which include employing a soybean plant as a source of plant breeding material comprising: using the soybean plant of claim 2 and wherein said plant breeding techniques are selected from the group consisting of: recurrent selection, backcrossing, pedigree breeding, restriction fragment length polymorphism enhanced selection, genetic marker enhanced selection, and transformation.

20. A soybean plant, or parts thereof, produced by the method of claim 19.

21. The soybean plant of claim 5, further comprising a single gene conversion.

22. The single gene conversion soybean plant of claim 21, where the gene is selected from the group consisting of: a transgenic gene, a dominant allele, and a recessive allele.

23. The single gene conversion soybean plant of claim 21, where the gene confers a characteristic selected from the group consisting of: herbicide resistance, insect resistance, resistance to bacterial, fungal, or viral disease, male sterility, and improved nutritional quality.

* * * * *